United States Patent [19]

Vedamuthu

[11] 4,339,464
[45] Jul. 13, 1982

[54] STABILIZER PRODUCING STREPTOCOCCUS THERMOPHILUS

[75] Inventor: Ebenezer R. Vedamuthu, Bradenton, Fla.

[73] Assignee: Microlife Technics, Inc., Sarasota, Fla.

[21] Appl. No.: 880,969

[22] Filed: Feb. 24, 1978

[51] Int. Cl.$^3$ .................. A23C 9/12; A23C 9/123; C12N 1/20; C12R 1/46
[52] U.S. Cl. ............................. 426/43; 426/34; 426/61; 435/253; 435/885
[58] Field of Search ............ 435/854, 253, 885; 426/34, 36, 38, 42, 43, 61

[56] References Cited

U.S. PATENT DOCUMENTS

| | | | |
|---|---|---|---|
| 2,119,599 | 6/1938 | Nordsiek | 426/43 |
| 3,025,165 | 3/1962 | Metzger | 426/43 X |
| 3,080,236 | 3/1963 | Ferguson, Jr. | 426/43 |
| 3,269,842 | 8/1966 | Mayer et al. | 426/43 |
| 3,539,363 | 11/1970 | Morgan et al. | 426/43 X |
| 3,563,760 | 2/1971 | Kuwabara | 426/43 |
| 3,876,808 | 4/1975 | Anderson | 426/43 X |
| 3,932,680 | 1/1976 | Egli et al. | 426/43 |
| 4,115,199 | 9/1978 | Porubcan et al. | 426/43 X |
| 4,156,019 | 5/1979 | Kondratenko et al. | 435/253 X |
| 4,243,684 | 1/1981 | Pruss et al. | 426/36 X |

OTHER PUBLICATIONS

Baumann et al., Freezing of Lactic Cultures, J. Da. Sci., vol. 49, 1966, pp. 259-264.
Webb, et al., Fundamentals of Dairy Chemistry, The Avi Publishing Co., Inc., Westport, Conn. 1965, pp. 734-735.

*Primary Examiner*—David M. Naff
*Attorney, Agent, or Firm*—Ian C. McLeod

[57] ABSTRACT

Naturally stabilized fermented milk products are prepared with a concentrate of *Streptococcus thermophilus* cells that produce a stabilizer in situ when cultured in milk. The concentrate is obtained by culturing the stabilizer-producing *Streptococcus thermophilus* in a growth medium including milk solids to obtain at least about $10^8$ cells per ml. The growth medium preferably contains maltose, sucrose, fructose or lactose which enhances stabilizer formation.

17 Claims, No Drawings

STABILIZER PRODUCING *STREPTOCOCCUS THERMOPHILUS*

DESCRIPTION OF THE INVENTION

The present invention relates to novel bacterial concentrates containing specially selected and grown strains of *Streptococcus thermophilus* and to the process for the preparation of such concentrates as well as to improved naturally acidified or fermented milk products prepared from such concentrates. In particular, the present invention relates to *Streptococcus thermophilus* concentrates which have an ability to provide a bacterially induced stabilizer in acidified milk products prepared with them.

Conventionally prepared yogurt has a characteristic lumpy texture that is not uniformly cohesive when stirred and also has a tendency to "whey-off", which is a separation or precipitation of the solids (essentially proteins) from the liquids. Various additive chemical stabilizers, such as plant gums, are used in an attempt to improve the stability and texture of the product. U.S. Pat. Nos. 3,080,236; 3,539,363; and 3,932,680 describe the use of various added stabilizers; however, there are still problems with lumpy texture and wheying-off in these products. Stabilizers are also added to the yogurt to maintain vegetables and/or fruits dispersed in the product which is a different problem than that relating to the texture of the yogurt alone.

Acidified milk products are commercially prepared using various strains of *Streptococcus thermophilus* alone or mixed with other lactic acid or flavor forming bacteria. Yogurt production requires the use of *S. thermophilus* with *Lactobacillus bulgaricus,* usually in an amount of about fifty (50) percent by proportion of each bacterium. U.S. Pat. Nos. 2,119,599; 3,025,165; 3,563,760 and 3,876,808 for instance describe various acidified milk products prepared with *S. thermophilus.* None of the *S. thermophilus* culture preparations described in these patents improve the stability or texture of the acidified milk products and the bacteria only promote acidity and flavor in these products.

Objects

It is therefore an object of the present invention to provide novel bacterial concentrates containing specially selected and grown strains of *Streptococcus thermophilus* which induce a stabilizer in situ in the acidified milk product, particularly yogurt. It is further an object of the present invention to provide preferred frozen concentrated cultures containing specially selected and grown stabilizer inducing *S. thermophilus* strains which can be used for a direct set of the milk, without the usual preliminary growth of the cells using bulk starters. Further still it is an object of the present invention to provide particular mixed bacterial cultures containing *S. thermophilus* and *Lactobacillus bulgaricus* for making a silky textured, smooth, naturally stabilized yogurt, which has no tendency to whey-off. These and other objects will become increasingly apparent by reference to the following description.

Description of the Invention

The present invention relates to the bacterial concentrates which comprises at least about $10^8$ cells per ml of an in situ stabilizer forming strain of *Streptococcus thermophilus* which has been grown in a growth medium containing milk solids or derivatives thereof such that the stabilizer can form in milk and which is in a form which provides for storage and shipment of the cells. Preferably the cells have been grown in a medium which in addition contains maltose, sucrose, fructose or lactose, which enhances the stabilizer formation in milk. The preferred *S. thermophilus* strain is NRRL-B-11,238 which is available to anyone who requests it by number from the United States Department of Agriculture, Northern Regional Research Center, 1815 North University St., Peoria, Ill. 61604. Other related stabilizer inducing strains can easily be detected by testing in milk. The preferred bacterial concentrates contain the in situ stabilizer forming *S. thermophilus* in admixture with a separately grown and concentrated *Lactobacillus bulgaricus* and are useful for making yogurt.

The bacterial concentrates are preferably frozen with a cryoprotective agent such as malt extract, a polyhydric alcohol, including sorbitol, mannitol or glycerol, or milk solids. Preferably a mixture of glycerol and malt extract is used. Lyophilization of the bacterial concentrates is not preferred because of the large population loss resulting from this preservation method.

The present invention also relates to the process for the preparation of a bacterial concentrate which comprises providing a bacterial growth medium containing milk solids or derivatives thereof as an essential ingredient along with other nutrients for growing *Streptococcus thermophilus* cells and; providing cells of an in situ stabilizer forming strain of *Streptococcus thermophilus* in the medium and growing the strain to a concentrate of at least about $10^8$ cells per ml at a temperature which does not exceed about 46° C., wherein the stabilizer is formed when the concentrate is added to milk and the cells incubated therein. As indicated, it has been found that the use of maltose, lactose, fructose or sucrose as well as milk solids (proteins) or derivatives thereof, such as casein, in the growth medium enhances the in situ stabilizer formation in the acidified milk product. In all cases, the presence of the mono- or disaccharides in the growth medium enhanced the in situ stabilizer formation which produced the novel smooth, silky, resilient body of the acidified milk product. The medium preferably contains at least about 0.01 percent maltose, sucrose, lactose and/or fructose and at least about 1.0 percent milk or derivatives by weight.

The bacteria are grown to a level of about $10^8$ cells per ml in the medium. They can be concentrated above the level of growth by various means, such as by centrifugation or dialysis of the growth medium, to a higher level, particularly above about $1.0 \times 10^{10}$ cells per ml. Usually if the cells are grown to a concentrate level of about $10^8$ cells per ml, it is sufficient for producing acidified milk products. The cells are grown at a temperature up to about 46° C. in order to induce the in situ stabilizer forming characteristic in milk. Above this growth temperature this characteristic is inconsistent.

The present invention further relates to the stabilized milk product which comprises milk containing a stabilizer induced in situ in the milk by a selected strain of *Streptococcus thermophilus* and which has been grown in a milk solids or derivatives thereof containing growth medium such that the milk product has and maintains a smooth, silky, viscous body at room temperatures. The product can be either of the refrigerated type where the bacteria are live or a product where the bacteria are killed which is shelf stable at room temperature.

Further still, the present invention relates to the method for producing a stabilized milk product which comprises providing in milk at least about $10^5$ cells per ml of the milk of an in situ stabilizer forming strain of *Streptococcus thermophilus* which has been grown to a concentration of at least about $10^8$ cells per ml in a growth medium containing milk solids or derivatives thereof; and incubating the cells in the milk to a temperature not exceeding 46° C. until the stabilizer is formed in the milk to provide a smooth, silky resilient viscous body in the milk. Where the *S. thermophilus* are mixed with *Lactobacillus bulgaricus* and incubated in the milk, the stabilized milk product is yogurt. The *S. thermophilus* can be mixed with *Leuconostoc cremoris, Streptococcus lactis, Streptococcus diacetylactis* or mixtures thereof for incubation in milk, such that the stabilized milk product is cultured buttermilk, sour cream, cultured milk or the like. The *Streptococcus thermophilus* mixed with *Leuconostoc cremoris, Streptococcus lactis* or *Streptococcus lactis* subspecies *diacetylactis* can be used to make cultured filled dressing or cultured imitation dressing with in situ stabilizer formation provided in the filled product contains an edible sugar such as sucrose, fructose or maltose and milk derived casein. The term "milk product" in this context also includes cultured filled or imitation dairy products.

Specific Description

The following examples relate to yogurt making cultures and acidified milk products. This is a preferred utility for the in situ stabilizer forming *S. thermophilus* of the present invention. There are a number of strains of this bacterium which have the in situ stabilizer forming property, providing they are grown properly.

EXAMPLE 1

From a large collection of authentic strains of *S. thermophilus* and *Lactobaccillus bulgaricus*, two strains were selected for the following reasons:

(1) The pair on culturing in heat-treated milk together produced desirable body and textural qualities particularly the desired silky and smooth body-texture.

(2) When grown together in milk, they were compatible and exhibited enhanced acid generating properties.

(3) The bacteria were adaptable to large scale fermentation and production in terms of mass propagation, concentration and freezing.

(4) The strains had cryostability.

The species used were: *S. thermophilus* NRRL-B-11,238 described previously and commercially available *L. bulgaricus* strains.

Propagation of Bacteria and Their Storage

The medium for *S. thermophilus* growth was as shown in Table I, where the percentages are by weight:

TABLE I

| Non-fat dry milk | 1% |
|---|---|
| Lactose | 2% |
| Yeast Extract | 1.5% |
| Maltose | 0.2% |
| Fructose | 0.2% |
| Na$_2$HPO$_4$ | 0.18% |
| KH$_2$PO$_4$ | 0.27% |

The medium was heat treated at 96.1° C. (205° F.) for 1 hour. The phosphates were added at 57.2° C. (135° F.). The pH of the medium was initially at pH 6.8. The pH was held static at pH 5.8 by addition of ammonia. The propagation temperature was 35° to 37.8° C. (95° to 100° F.). Propagation was continued until the carbohydrates were exhausted (12 to 14 hr.). The propagation temperature was important in order to maintain the specific texture-producing characteristic in milk. The preferred temperature range is 35° to 46° C. (95° to 115° F.).

The medium and conditions of growth for *L. bulgaricus* were as conventionally known in the prior art. The cells were grown to a concentration of about $1.5 \times 10^9$ cells per ml.

Making up the Composite Culture

After mechanical separation by centrifugation of cells of each strain from the growth medium, the bacterial concentrates were mixed in a 1:1 ratio by weight of the concentrates with the cryoprotective agents, glycerol and malt extract. The bacterial cells of each strain were each at a concentration of about $5 \times 10^9$ to $10 \times 10^9$ cells per ml. After packaging, the mixed culture was quick-frozen and stored below −29° C. (−20° F.).

The following Example 2 compares a prior art yogurt with the yogurt of the present invention without any added stabilizers or flavorings. The object was to compare the consistency of the product of the present invention with a prior art yogurt.

EXAMPLE 2

A one percent (1%) by weight fat containing milk fortified with one percent (1%) non-fat milk solids (M.S.N.F.) by weight was used. The milk was steamed for 1 hour and then cooled to 35° C. to 37.8° C. (95° F. to 100° F.). The thawed culture of Example 1 was added directly to one milk sample and a standard prior art commercial culture was added to another sample each at a level of about $10^6$ cells per ml. Both cultures contained approximately the same proportions of *Streptococcus thermophilus* and *Lactobacillus bulgaricus*. The milk and culture mixture was incubated for 14 to 16 hours and then was examined organoleptically for texture. The product of the invention had a smooth, silky, resilient texture and consistency, while the prior art product had the usual lumpy texture. When the products were temperature stressed by being allowed to stand at room temperatures for one (1) hour, the prior art product wheyed-off while the product of the present invention exhibited no wheying-off. This was found to be the case with repeated tests of the same product which was stirred, cooled and re-stressed after varying lengths of time.

In the following Examples 3 to 5 added stabilizer, which was a mixture of gelatin and agar-agar, was optionally included in order to facilitate the later incorporation of fruits and vegetables in the yogurt, which is the usual commercial practice. Where the product does not contain such fruits or vegetables, the added stabilizer can be eliminated as in Example 2. With or without an added stabilizer there is a distinct difference in texture between the prior art products and those of the present invention. The percentages in Examples 3 to 5 are by weight.

EXAMPLE 3

Yogurt drink was made by culturing a mixture that meets the proposed Federal Regulatory Standards (Federal Register Vol. 42, No. 112- June 10, 1977) for yogurt with reference to butterfat (3.25%) and nonfat milk solids (M.S.N.F., 8.25%). The culture used in the fermentation contained the *Streptococcus thermophilus* and *Lactobacillus bulgaricus* mixture of Example 1. The final product had a titratable acidity not less than 0.5% expressed as lactic acid.

The formulation used was:

| Butterfat | 3.5% |
|---|---|
| M.S.N.F | 8.25% (can vary from 8.25 to 10.0%) |
| Stabilizer | 0.2%–0.3% |
| Cane Sugar | 4.0%–10.0% |

EXAMPLE 4

Lowfat yogurt drink was made by culturing a mixture that meets the proposed Federal standards for lowfat yogurt with reference to butterfat (range of 0.5 to 2.0%) and M.S.N.F. (8.25%). The mixture was fermented with the yogurt culture of Example 1 to a titratable acidity not less than 0.5% expressed as lactic acid.

The formulation for lowfat yogurt drink was:

| Butterfat | 0.5–2.0% |
|---|---|
| M.S.N.F | 0.25% (can vary from 8.25 to 10.0% |
| Stabilizer | 0.2%–0.3% |
| Cane Sugar | 4.0%–10.0% |

EXAMPLE 5

Nonfat yogurt drink was made by culturing a mixture meeting the proposed Federal standards for nonfat yogurt with reference to butterfat (not more than 0.5%) and M.S.N.F. (at least 8.25%). It was made by culturing with the starter of Example 1 and had a titratable acidity of not less than 0.5%, expressed as lactic acid.

The formulation for nonfat yogurt drink was:

| Fresh skim milk | (should have at least 8.5% solids) |
|---|---|
| M.S.N.F | 1.0–1.5% |
| Butterfat | (no more than 0.5%) |
| Stabilizer | 0.2%–0.3% |
| Cane Sugar | 4.0%–10.0% |

Preparation of the Acidified Milk Products of Examples 3, 4 and 5

FIRST PHASE

1. Fresh milk was standardized to the appropriate butterfat level depending upon the above category of liquid yogurt desired.
2. If necessary the milk was fortified with grade A nonfat dry milk to obtain the desired M.S.N.F. level and mixed well. The steam valves in the vat were opened for heating.
3. The stabilizer was combined with dry cane sugar and added to the milk through a powder funnel before the temperature of milk reached 43.3° C. (110° F.).
4. After the temperature reached 62.8° C. (145° F.), the mixture was homogenized at 211 kg per sq. centimeter (3,000 psi) in a single stage homogenizer.
5. The heating was continued until the mixture attained 82.2° C. (180° F.) and the mixture was held at this temperature for 30 minutes.
6. Depending on the time schedules desired, two time-temperature combinations were used for incubation per A and B below. The 37.8° C. (100° F.) incubation temperature is recommended for obtaining a top quality product.

A. LOW TEMPERATURE-OVERNIGHT INCUBATION

The milk mixture (5 above) was cooled at 37.8° C. (100° F.). The frozen culture(s) in a sealed container was removed from the freezer, and the container, containing 170 grams of culture for 300 gallons of milk mixture, was placed in 37.8° C. (100° F.) warm water containing 100 ppm available chlorine. After five minutes, the hands and arms were rinsed with chlorinated water and one container at a time was removed from water. The culture was added directly into the fermentation tank and the mixture agitated exactly 30 minutes. The temperature of the mixture was maintained at 37.8° C. (100° F.) until the pH dropped to 4.3 (about 12 to 15 hours).

B. HIGH TEMPERATURE-SHORT TIME INCUBATION

The milk mixture (5 above) was cooled at 45° C. (113° F.). The frozen culture was removed from the freezer and the container placed in 37.8° C. (100° F.) warm water containing 100 ppm available chlorine. After five (5) minutes, the hands and arms were rinsed with chlorinated water and one container at a time was removed from water. The culture was added directly into fermentation tank and agitated for exactly 30 minutes. The temperature was maintained at 45° C. (113° F.) until pH dropped to 4.3 (about 8 to 9 hours).

SECOND PHASE

6. The cooling jacket was activated and the mixture cooled with slow agitation to 32.2° C. (90° F.). At this stage the desired flavorings (fruit and/or vegetable) were added and mixed with the agitator set at a medium setting.
7. The mixture was cooled rapidly to 4.4° C. (40° F.).
8. Using a positive pump, the mixture was pumped to a filler machine and packaged in the final container.
9. The product was held in a 3.3° C. (38° F.) cooler overnight to develop the desired body, texture and mouthfeel.

As can be seen from the foregoing description, novel yogurt products can be produced. In a like manner, various acidified milk products with an improved texture can be prepared, such as buttermilk, sour cream or cultured filled or containing dressings.

I claim:

1. A process for the preparation of a bacterial concentrate which produces a stabilizer when the bacteria are incubated in milk to produce a naturally stabilized fermented milk product having a smooth, silky, viscous body at room temperature which comprises:
providing cells of *Streptococcus thermophilus* NRRL-B-11,238 in a growth medium including milk solids or derivatives thereof which cause the bacteria to form the stabilizer when incubated in milk and growing the cells to produce a concentrate of at least about $10^8$ cells per ml at a temperature which does not exceed about 46° C.

2. The process of claim 1 wherein the cells are concentrated further to above about $10 \times 10^9$ cells per ml.

3. The process of claim 1 wherein the cells are concentrated above the concentration to which they are grown in the medium.

4. The process of claim 1 wherein the growth medium contains a sugar selected from maltose, lactose, fructose and sucrose.

5. The process of claim 1 wherein the medium contains at least about 0.01 percent by weight maltose, fructose or sucrose and at least about 1.0 percent by weight milk or milk derivative wherein the cells are grown at a temperature between 35° C. to 46° C. and wherein the bacterial concentrate is frozen for storage and shipment.

6. The process of claim 1 wherein the cell growth temperature is between about 35° C. to 46° C.

7. The process of claim 1 wherein the concentrate is mixed with a strain of *Lactobacillus bulgaricus* to produce a yogurt making culture.

8. A bacterial concentrate which produces a stabilizer when incubated in milk to produce a naturally stabilized fermented milk product having a smooth, silky, viscous body at room temperature, which comprises:

at least about $10^8$ cells per ml of *Streptococcus thermophilus* NRRL-B-11,238 which has been grown in a growth medium containing milk solids or derivatives thereof which cause the bacteria to form the stabilizer when incubated in milk and which concentrate is in a form which provides for storage and shipment of the cells.

9. The concentrate of claim 8 wherein the cells in the concentrate have been grown in a medium containing at least about 0.01 percent by weight of a sugar selected from maltose, lactose, fructose and sucrose, and containing at least about 1.0 percent by weight milk or milk derivative, wherein the cells are grown at a temperature between 35° C. and 46° C. and wherein the concentrate has been frozen for storage and shipment.

10. The concentrate of claim 8 wherein the concentrate is frozen with a cryoprotective agent for the cells.

11. The concentrate of claim 10 wherein the cryoprotective agent is a mixture of glycerol and malt extract.

12. The concentrate of claim 8 wherein the strain of *Streptococcus thermophilus* is in admixture with a separately grown concentrate of *Lactobacillus bulgaricus*.

13. The concentrate of claim 8 wherein the concentrate is admixed with a strain of *Lactobacillus bulgaricus* to produce a yogurt making culture.

14. A method for producing a naturally stabilized fermented milk product having a smooth, silky, viscous body at room temperature which comprises:
  (a) providing in milk at least about $10^5$ cells per ml of the milk of *Streptococcus thermophilus* NRRL-B-11,238 which produces a stabilizer in situ when grown in milk and which has been previously grown to a concentration of at least about $10^8$ cells per ml at a temperature between about 35° C. and 46° C. in a growth medium containing at least about 1.0 percent by weight of milk solids or derivatives thereof which cause the bacteria to form the stabilizer when incubated in milk and at least about 0.01 percent by weight of maltose, lactose, fructose or sucrose; and
  (b) incubating the cells in the milk at a temperature not exceeding about 46° C. until the stabilizer is formed in the milk to provide a smooth, silky resilient viscous body in the milk.

15. The method of claim 14 wherein the *Streptococcus thermophilus* cells are mixed with *Lactobacillus bulgaricus* such that the stabilized milk product is yogurt.

16. A method for producing a naturally stabilized fermented milk product having a smooth, silky, viscous body at room temperature which comprises:
  (a) providing in a milk product at least about $10^5$ cells per ml of the milk product of *Streptococcus thermophilus* NRRL-B-11,238 which produces a stabilizer in situ when grown in milk and which has previously been grown to a concentration of at least about $10^8$ cells per ml in a growth medium containing milk solids or derivatives thereof which cause the bacteria to form the stabilizer when incubated in milk; and
  (b) incubating the cells in the milk product at a temperature not exceeding about 46° C. until the stabilizer is formed in the milk product to provide a smooth, silky resilient viscous body in the milk product.

17. A naturally stabilized fermented milk product produced without added stabilizers and which does not whey-off prepared by the method of claim 14 or 16.

* * * * *